(12) United States Patent
Yoshida et al.

(10) Patent No.: US 6,593,488 B1
(45) Date of Patent: Jul. 15, 2003

(54) 4-FLUORO-3-OXOCARBOXYLIC ESTERS AND PROCESS FOR PRODUCING THE SAME

(75) Inventors: Hiroshi Yoshida, Ube (JP); Kiyoshi Ohmori, Ube (JP); Kensaku Fuse, Ube (JP); Kazuhiro Morita, Ube (JP); Yoshitaka Onduka, Ube (JP); Naoyuki Yokota, Ube (JP)

(73) Assignee: UBE Industries, Ltd., Yamaguchi (JP)

( * ) Notice: Subject to any disclaimer, the term of this patent is extended or adjusted under 35 U.S.C. 154(b) by 0 days.

(21) Appl. No.: 09/581,310

(22) PCT Filed: Dec. 4, 1998

(86) PCT No.: PCT/JP98/05473
§ 371 (c)(1),
(2), (4) Date: Jun. 12, 2000

(87) PCT Pub. No.: WO99/31044
PCT Pub. Date: Jun. 24, 1999

(30) Foreign Application Priority Data

Dec. 12, 1997 (JP) ................................. 9-342342

(51) Int. Cl.⁷ ................... C07C 69/66; C07C 69/72
(52) U.S. Cl. .................. 560/53; 560/174; 560/178
(58) Field of Search ................. 560/62, 178, 174, 560/53

(56) References Cited

FOREIGN PATENT DOCUMENTS

| DE | 2329817 A1 | * 1/1974 |
| JP | 06306056 | * 11/1994 |

OTHER PUBLICATIONS

Svendsen et al, Naturally Occurring Lactones and Lactams. V. Halogenated .beta.–keto Esters as Starting Materials for the Synthesis of Tetronic Acids, 1973, Tetrahedron, 29, pp. 4251–4258.*
Solomons Organic Chemistry, 5th edition, 1992, John Wiley and Sons, New York, pp. 888–894.*
Crombie et al., J. Chem. Soc., vol. 2, No. 1, pp. 333–343 (1987).
Ohta et al., Synethesis, vol. 1, pp. 45–48 (1985).
Database Chem. Abs.; Chemical Abstracts Service, Columbus, Ohio; Kudo, Sachio et al; Database Accession No. 122:187603 CA XP002159757 & Abstract of JP 06306056 A (Nov. 1, 1994).

* cited by examiner

Primary Examiner—Johann Richter
Assistant Examiner—Paul A. Zucker
(74) Attorney, Agent, or Firm—Birch, Stewart, Kolasch, & Birch, LLP

(57) ABSTRACT

The present invention is to provide 4-fluoro-3-oxocarboxylates represented by the following formula (1):

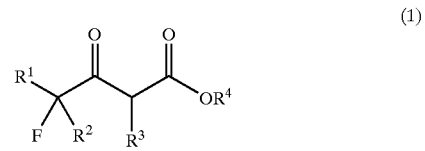

(1)

wherein $R^1$ represents an alkyl group or an aryl group;

$R^2$ and $R^3$ each represent a hydrogen atom or an alkyl group;

and $R^4$ represents an alkyl group, and a process for preparing a 4-fluoro-3-oxocarboxylate represented by the above formula (1), which comprises allowing a 2-fluorocarboxylate represented by the following formula (2):

wherein $R^1$ and $R^2$ have the same meanings as defined above;

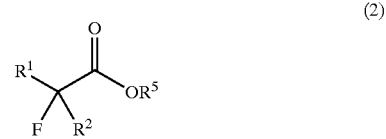

(2)

and $R^5$ represents an alkyl group, to react with a carboxylate represented by the following formula (3):

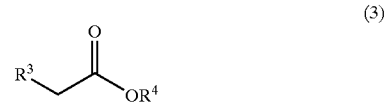

(3)

wherein $R^3$ and $R^4$ have the same meanings as defined above, in the presence of a base.

8 Claims, No Drawings

4-FLUORO-3-OXOCARBOXYLIC ESTERS AND PROCESS FOR PRODUCING THE SAME

This application is the national phase under 35 U.S.C. §371 of PCT International Application. No. PCT/JP98/05473 which has an International filing date of Dec. 4, 1998, which designated the United States of America.

TECHNICAL FIELD

The present Invention relates to novel 4-fluoro-3-oxocarboxylates which are important as synthetic intermediates of aminopyrimidine derivatives (Japanese Provisional Patent Publications No. 230036/1993, No. 25187/1994, No. 116247/1994, No. 247939/1994, and No. 258223/1995) useful as an insecticide, acaricide, fungicide or nematocide, and the process for producing the same.

BACKGROUND ART

The 4-fluoro-3-oxocarboxylates of the present invention are novel compounds.

An object of the present invention is to provide a process for industrially producing 4-fluoro-3-oxocarboxylates which are novel compounds and important as synthetic intermediates of aminopyrimidine derivatives (Japanese Provisional Patent Publications No. 230036/1993, No. 25187/1994, No. 116247/1994, No. 247939/1994 and No. 258223/1995) useful as an insecticide, acaricide, fungicide or nematocide with a low cost and good yield.

The present inventors have studied to solve the above-mentioned problem, and as a result, they have found that 4-fluoro-3-oxocarboxylates which are novel compounds become an important synthetic intermediate for the above-mentioned useful aminopyrimidine derivatives, and established the preparation process to accomplish the present invention.

DISCLOSURE OF THE INVENTION

That is, the first invention relates to a 4-fluoro-3-oxocarboxylate represented by the following formula (1):

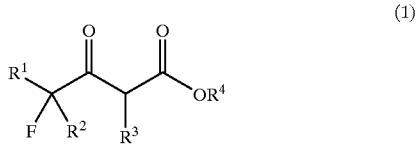

(1)

wherein $R^1$ represents an alkyl group or an aryl group; $R^2$ and $R^3$ each represent a hydrogen atom or an alkyl group; and $R^4$ represents an alkyl group.

The second invention relates to a process for preparing a 4-fluoro-3-oxocarboxylate represented by the above formula 1), which comprises allowing a 2-fluorocarboxylate represented by the following formula (2):

(2)

wherein $R^1$ and $R^2$ have the same meanings as defined above;

and $R^5$ represents an alkyl group, to react with a carboxylate represented by the following formula (3):

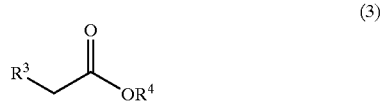

(3)

wherein $R^3$ and $R^4$ have the same meanings as defined above, in the presence of a base.

BEST MODE FOR CARRYING OUT THE INVENTION

In the following, the present invention is explained in detail.

$R^1$ to $R^5$ in the 4-fluoro-3-oxocarboxylate (Compound (1)) which is an objective compound and in the starting materials for the preparation thereof (the compound (2) represented by the formula (2), and the compound (3) represented by the formula (3)) are as mentioned below.

As $R^1$, there may be mentioned an alkyl group and an aryl group.

As the alkyl group of $R^1$, there may be mentioned a straight or branched alkyl group having 1 to 10 carbon atoms; preferably 1 to 4 carbon atoms, more preferably a methyl group, an ethyl group, an n-propyl group and an n-butyl group.

As the aryl group of $R^1$, there may be mentioned an aryl group having 6 to 10 carbon atoms; preferably a phenyl group.

As $R^2$ and $R^3$, there may be mentioned a hydrogen atom and an alkyl group.

As the alkyl group of $R^2$ and $R^3$, there may be mentioned a straight or branched alkyl group having 1 to 10 carbon atoms; preferably 1 to 4 carbon atoms. As $R^2$, a straight alkyl group having 1 to 4 carbon atoms is preferred, and particularly preferred is a methyl group. As $R^3$, a straight alkyl group having 1 to 4 carbon atoms is preferred, and particularly preferred is a methyl group.

As $R^4$ and $R^5$, there may be mentioned an alkyl group.

As the alkyl group of $R^4$ and $R^5$, there may be mentioned a straight or branched alkyl group having 1 to 10 carbon atoms; preferably 1 to 4 carbon atoms. As $R^4$, a methyl group, an ethyl group or an n-butyl group is more preferred. As $R^5$, a methyl group, an ethyl group or an n-butyl group is more preferred.

The compound (1) of the present invention is exemplified below. There may be mentioned methyl 4-fluoro-3-oxopentanoate,
methyl 4-fluoro-3-oxohexanoate,
methyl 4-fluoro-3-oxoheptanoate,
methyl 4-fluoro-3-oxooctanoate,
methyl 4-fluoro-2-methyl-3-oxopentanoate,
methyl 4-fluoro-2-methyl-3-oxohexanoate,
methyl 4-fluoro-2-methyl-3-oxoheptanoate,
methyl 4-fluoro-2-methyl-3-oxooctanoate,
methyl 4-fluoro-4-methyl-3-oxopentanoate,
methyl 4-fluoro-4-methyl-3-oxohexanoate,
methyl 4-fluoro-4-methyl-3-oxoheptanoate,
methyl 4-fluoro-4-methyl-3-oxooctanoate,
methyl 4-fluoro-2,4-dimethyl-3-oxopentanoate,
methyl 4-fluoro-3-oxo-4-phenylbutanoate,
methyl 4-fluoro-2-methyl-3-oxo-4-phenylbutanoate,
ethyl 4-fluoro-3-oxopentanoate, ethyl 4-fluoro-3-oxohexanoate,
ethyl 4-fluoro-3-oxoheptanoate,
ethyl 4-fluoro-3-oxooctanoate,
ethyl 4-fluoro-2-methyl-3-oxopentanoate,
ethyl 4-fluoro-2-methyl-3-oxohexanoate,
ethyl 4-fluoro-2-methyl-3-oxoheptanoate,
ethyl 4-fluoro-2-methyl-3-oxooctanoate,
ethyl 4-fluoro-4-methyl-3-oxopentanoate,
ethyl 4-fluoro-4-methyl-3-oxohexanoate,
ethyl 4-fluoro-4-methyl-3-oxoheptanoate,
ethyl 4-fluoro-4-methyl-3-oxooctanoate,
ethyl 4-fluoro-2,4-dimethyl-3-oxopentanoate,
ethyl 4-fluoro-3-oxo-4-phenylbutanoate,
ethyl 4-fluoro-2-methyl-3-oxo-4-phenylbutanoate,
propyl 4-fluoro-3-oxopentanoate,
propyl 4-fluoro-3-oxohexanoate,
propyl 4-fluoro-3-oxoheptanoate,
propyl 4-fluoro-3-oxooctanoate,
propyl 4-fluoro-2-methyl-3-oxopentanoate,
propyl 4-fluoro-2-methyl-3-oxohexanoate,
propyl 4-fluoro-2-methyl-3-oxoheptanoate,
propyl 4-fluoro-2-methyl-3-oxooctanoate,
propyl 4-fluoro-4-methyl-3-oxopentanoate,
propyl 4-fluoro-2,4-dimethyl-3-oxopentanoate,
propyl 4-fluoro-3-oxo-4-phenylbutanoate,
propyl 4-fluoro-2-methyl-3-oxo-4-phenylbutanoate,
butyl 4-fluoro-3-oxopentanoate,
butyl 4-fluoro-3-oxohexanoate,
butyl 4-fluoro-3-oxoheptanoate,
butyl 4-fluoro-3-oxooctanoate,
butyl 4-fluoro-2-methyl-3-oxopentanoate,
butyl 4-fluoro-2-methyl-3-oxohexanoate,
butyl 4-fluoro-2-methyl-3-oxoheptanoate,
butyl 4-fluoro-2-methyl-3-oxooctanoate,
butyl 4-fluoro-4-methyl-3-oxopentanoate,
butyl 4-fluoro-2,4-dimethyl-3-oxopentanoate,
butyl 4-fluoro-3-oxo-4-phenylbutanoate,
butyl 4-fluoro-2-methyl-3-oxo-4-phenylbutanoate,
isopropyl 4-fluoro-3-oxopentanoate,
isopropyl 4-fluoro-3-oxohexanoate,
isopropyl 4-fluoro-3-oxoheptanoate,
isopropyl 4-fluoro-3-oxooctanoate,
isopropyl 4-fluoro-2-methyl-3-oxopentanoate,
isopropyl 4-fluoro-2-methyl-3-oxohexanoate,
isopropyl 4-fluoro-2-methyl-3-oxoheptanoate,
isopropyl 4-fluoro-2-methyl-3-oxooctanoate,
isopropyl 4-fluoro-4-methyl-3-oxopentanoate,
isopropyl 4-fluoro-2,4-dimethyl-3-oxopentanoate,
isopropyl 4-fluoro-3-oxo-4-phenylbutanoate,
isopropyl 4-fluoro-2-methyl-3-oxo-4-phenylbutanoate,
isobutyl 4-fluoro-3-oxopentanoate,
isobutyl 4-fluoro-3-oxohexanoate,
isobutyl 4-fluoro-3-oxoheptanoate,
isobutyl 4-fluoro-3-oxooctanoate,
isobutyl 4-fluoro-2-methyl-3-oxopentanoate,
isobutyl 4-fluoro-2-methyl-3-oxohexanoate,
isobutyl 4-fluoro-2-methyl-3-oxoheptanoate,
isobutyl 4-fluoro-2-methyl-3-oxooctanoate,
isobutyl 4-fluoro-4-methyl-3-oxopentanoate,
isobutyl 4-fluoro-2,4-dimethyl-3-oxopentanoate,
isobutyl 4-fluoro-3-oxo-4-phenylbutanoate, and
isobutyl 4-fluoro-2-methyl-3-oxo-4-phenylbutanoate.

Among the compounds as mentioned above, preferred as the compound (1) are exemplified below. They are methyl 4-fluoro-3-oxopentanoate,
methyl 4-fluoro-3-oxohexanoate,
methyl 4-fluoro-3-oxoheptanoate,
methyl 4-fluoro-3-oxooctanoate,
methyl 4-fluoro-2-methyl-3-oxopentanoate,
methyl 4-fluoro-2-methyl-3-oxohexanoate,
methyl 4-fluoro-2-methyl-3-oxoheptanoate,
methyl 4-fluoro-2-methyl-3-oxooctanoate,
methyl 4-fluoro-4-methyl-3-oxooctanoate,
methyl 4-fluoro-2,4-dimethyl-3-oxopentanoate,
methyl 4-fluoro-3-oxo-4-phenylbutanoate,
methyl 4-fluoro-2-methyl-3-oxo-4-phenylbutanoate,
ethyl 4-fluoro-3-oxopentanoate,
ethyl 4-fluoro-3-oxohexanoate,
ethyl 4-fluoro-3-oxoheptanoate,
ethyl 4-fluoro-3-oxooctanoate,
ethyl 4-fluoro-2-methyl-3-oxopentanoate,
ethyl 4-fluoro-2-methyl-3-oxohexanoate,
ethyl 4-fluoro-2-methyl-3-oxoheptanoate,
ethyl 4-fluoro-2-methyl-3-oxooctanoate,
ethyl 4-fluoro-4-methyl-3-oxopentanoate,
ethyl 4-fluoro-2,4-dimethyl-3-oxopentanoate,
ethyl 4-fluoro-3-oxo-4-phenylbutanoate,
ethyl 4-fluoro-2-methyl-3-oxo-4-phenylbutanoate,
butyl 4-fluoro-3-oxopentanoate,
butyl 4-fluoro-3-oxohexanoate,
butyl 4-fluoro-3-oxoheptanoate, and
butyl 4-fluoro-3-oxooctanoate.

The compound (2) (2-fluorocarboxylate) to be used can be easily obtained from a mesitylate of corresponding 2-hydroxycarboxylate and potassium fluoride (Tetrahedron Lett., 1993, p. 293, Tetrahedron; Asymmetry, 1994, p. 981).

The compound (3) (a starting ester represented by the formula (3)) to be used is a compound which is an industrially available.

Amounts to be used of the starting compounds are 1-fold mol or more of the compound (3) based on the amount of the compound (2); preferably 1 to 3-fold mol.

A base to be used is preferably alkali metal alkoxide such as sodium methoxide, sodium ethoxide, sodium butoxide, potassium t-butoxide, etc., and an alkali metal hydride such as lithium hydride, sodium hydride, potassium hydride, etc., more preferably sodium methoxide or sodium hydride.

An amount of the base to be used is 1-fold mol or more based on the compound (2); preferably 1 to 3-fold mol.

Synthesis of the compound (1) can be carried out without a solvent or in the presence of a solvent.

As the solvent, it is not particularly limited so long as it is not participate in the present reaction, and there may be mentioned, for example, an ether such as diethyl ether, tetrahydrofuran, 1,2-dimethoxyethane, 1,4-dioxane, etc.; an amide such as N,N-dimethylformamide, N,N-dimethylacetamide, etc.; and an aromatic hydrocarbons such as toluene, xylene, etc. And these solvents may be used singly or in combination of two or more.

An amount of the solvent to be used is 0 to 50-fold volume based on the compound (2); preferably 2 to 20-fold volume.

A temperature for synthesis of the compound (1) is 0 to 80° C.; preferably 30 to 60° C.

A reaction time for synthesis of the compound (1) may vary depending on the concentration, temperature and amounts to be used; and generally 0.5 to 10 hours.

The desired compound (1) prepared as mentioned above can be subjected to the conventional post-treatments such as washing, extraction, concentration, etc., and depending on necessity, can be purified by the known means such as distillation or various kinds of chromatography, etc.

From the thus obtained compound (1), aminopyrimidine derivatives useful as an insecticide, acaricide, fungicide or nematocide can be obtained.

Synthetic example of the aminopyrimidine derivatives is shown below. Incidentally, in this synthesis, methyl 4-fluoro-3-oxopentanoate which is one of the compound (1) is cyclized by formamidine and further chlorinating the 5-position and the 4-position to obtain 4,5-dichloro-6-(1-fluoroethyl)pyrimidine which is an important synthetic intermediate of useful aminopyrimidine derivatives.

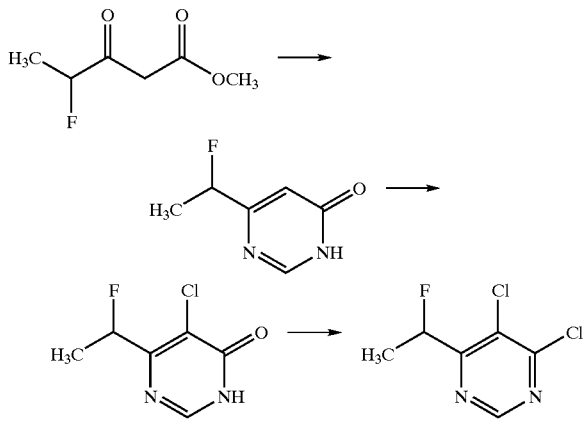

EXAMPLES

In the following, the present invention is explained specifically by referring to examples, but these examples do not limit the scope of the present invention.

Example 1

Synthesis of methyl 4-fluoro-3-oxopentanoate

To a liquor in which 1.31 g of 62.8% sodium hydride was suspended in 10 ml of tetrahydrofuran was added dropwise a mixed solution comprising 2.00 g of methyl 2-fluoropropionate and 2.10 g of methyl acetate over 10 minutes, and the mixture was then heated at 30 to 35° C. for 4 hours.

After completion of the reaction, the mixture was cooled to room temperature, neutralized with 1N-hydrochloric acid and the liquids were separated. The organic layer was quantitated by the gas chromatography internal standard method to find out that 2.57 g of methyl 4-fluoro-3-oxopentanoate was formed (yield: 92%).

This organic layer was concentrated under reduced pressure, and distilled under reduced pressure to obtain 2.03 g of methyl 4-fluoro-3-oxopentanoate.

Boiling point: 80 to 81° C./24 to 25 mmHg

Mass analysis value: CI-MS m/e=149 (m+1)

$^1$H-NMR (CDCl$_3$) δ (ppm): 1.47 to 1.60 (3H, m), 3.66 to 3.67 (1.7H, d), 3.76 to 3.77 (3H, d), 4.87 to 5.12 (1H, m), 5.33 (0.15H, s), 11.80 to 12.00 (0.15H, bs)

According to $^1$H-NMR analysis, it could be confirmed to exist a keto-enol form.

Example 2

Synthesis of methyl 4-fluoro-3-oxopentanoate

To a liquor in which 2.32 g of powder sodium methoxide was suspended in 10 ml of tetrahydrofuran was added dropwise a mixed solution comprising 2.00 g of methyl 2-fluoropropionate and 2.80 g of methyl acetate over 10 minutes, and the mixture was then heated at 50 to 60° C. for 5 hours.

After completion of the reaction, the mixture was cooled to room temperature, neutralized with 1N-hydrochloric acid and the liquids were separated. The organic layer was quantitated by the gas chromatography internal standard method to find out that 2.36 g of methyl 4-fluoro-3-oxopentanoate was formed (yield: 84%).

This organic layer was concentrated under reduced pressure, and distilled under reduced pressure to obtain 1.86 g of methyl 4-fluoro-3-oxopentanoate.

Example 3

Synthesis of ethyl 4-fluoro-3-oxopentanoate

To a liquor in which 1.28 g of 62.8% sodium hydride was suspended in 10 ml of tetrahydrofuran was added dropwise a mixed solution comprising 2.00 g of ethyl 2-fluoropropionate and 1.91 g of ethyl acetate over 10 minutes, and the mixture was then heated at 35 to 40° C. for 4 hours.

After completion of the reaction, the mixture was cooled to room temperature, neutralized with 1N-hydrochloric acid and the liquids were separated. The organic layer was quantitated by the gas chromatography internal standard method to find out that 2.35 g of ethyl 4-fluoro-3-oxopentanoate was formed (yield: 87%).

This organic layer was concentrated under reduced pressure, and distilled under reduced pressure to obtain 1.73 g of ethyl 4-fluoro-3-oxopentanoate.

Boiling point: 38 to 41° C./2 mmHg

Mass analysis value: CI-MS m/e=163 (m+1)

$^1$H-NMR (CDCl$_3$) δ (ppm): 1.26 to 1.32 (3H, m), 1.47 to 1.60 (3H, m), 3.63 to 3.64 (1.72H, d), 4.18 to 4.26 (2H, m), 4.86 to 5.12 (1H, m), 5.31 (0.14H, s), 12.02 (0.14H, s)

According to $^1$H-NMR analysis, it could be confirmed to exist a keto-enol form.

Example 4

Synthesis of methyl and ethyl 4-fluoro-3-oxopentanoates

To a liquor in which 1.26 g of 63.7% sodium hydride was suspended in 10 ml of tetrahydrofuran was added dropwise a mixed solution comprising 2.00 g of ethyl 2-fluoropropionate and 1.86 g of methyl acetate over 10 minutes, and the mixture was then heated at 30 to 35° C. for 4 hours.

After completion of the reaction, the mixture was cooled to room temperature, neutralized with 1N-hydrochloric acid and the liquids were separated. The organic layer was quantitated by the gas chromatography internal standard method to find out that 1.43 g (yield: 58%) of methyl 4-fluoro-3-oxopentanoate and 0.95 g (yield: 35%) of ethyl 4-fluoro-3-oxopentanoate were formed (total yield: 93%).

Example 5

Synthesis of butyl 4-fluoro-3-oxopentanoate

To a liquor in which 15.41 g of 63.7% sodium hydride was suspended in 150 ml of tetrahydrofuran was added dropwise a mixed solution comprising 29.86 g of butyl 2-fluoropropionate and 35.31 g of butyl acetate over 90 minutes, and the mixture was then heated at 45 to 55° C. for 6 hours.

After completion of the reaction, the mixture was cooled to room temperature, neutralized with 1N-hydrochloric acid and the liquids were separated. The organic layer was quantitated by the gas chromatography internal standard method to find out that 23.79 g of butyl 4-fluoro-3-oxopentanoate was formed (yield: 62%).

This organic layer was concentrated under reduced pressure, and distilled under reduced pressure to obtain 20.00 g of butyl 4-fluoro-3-oxopentanoate.

Boiling point: 92 to 95° C./7 to 8 mmHg

Mass analysis value: CI-MS m/e=191 (m+1)

$^1$H-NMR (CDCl$_3$) δ (ppm): 0.91 to 0.97 (3H, m), 1.31 to 1.69 (7H, m), 3.63 to 3.65 (1.7H, m), 4.13 to 4.19 (2H, m), 4.86 to 5.12 (1H, m), 5.32 (0.15H, s), 11.70 to 12.30 (0.15H, bs)

According to $^1$H-NMR analysis, it could be confirmed to exist a keto-enol form.

Example 6

Synthesis of ethyl 4-fluoro-4-methyl-3-oxopentanoate

To a liquor in which 13.11 g of 63.7% sodium hydride was suspended in 115 ml of tetrahydrofuran was added dropwise a mixed solution comprising 23.02 g of ethyl 2-fluoro-2-methylpropionate and 22.85 g of ethyl acetate over 75 minutes, and the mixture was then heated at 35 to 45° C. for 4 hours.

After completion of the reaction, the mixture was cooled to room temperature, neutralized with 1N-hydrochloric acid and the liquids were separated. The organic layer was quantitated by the gas chromatography internal standard method to find out that 23.75 g of ethyl 4-fluoro-4-methyl-3-oxopentanoate was formed (yield: 78%).

This organic layer was concentrated under reduced pressure, and distilled under reduced pressure to obtain 21.42 g of ethyl 4-fluoro-4-methyl-3-oxopentanoate.

Boiling point: 65 to 70° C./10 mmHg

Mass analysis value: CI-MS m/e=177 (m+1)

$^1$H-NMR (CDCl$_3$) δ (ppm): 1.24 to 1.33 (3H, m), 1.43 to 1.67 (6H, m), 3.65 to 3.67 (1.8H, d), 4.17 to 4.25 (2H, m), 5.35 (0.1H, s), 11.90 to 12.40 (0.1H, bs)

According to $^1$H-NMR analysis, it could be confirmed to exist a keto-enol form.

Example 7

Synthesis of ethyl 4-fluoro-3-oxo-4-phenylbutanoate

To a liquor in which 0.75 g of 63.7% sodium hydride was suspended in 10 ml of tetrahydrofuran was added dropwise a mixed solution comprising 1.81 g of ethyl α-fluorophenylacetate and 1.32 g of ethyl acetate over 10 minutes, and the mixture was then heated at 35 to 40° C. for 3 hours.

After completion of the reaction, the mixture was cooled to room temperature, neutralized with 1N-hydrochloric acid and the liquids were separated. The organic layer was quantitated by the gas chromatography internal standard method to find out that 1.63 g of ethyl 4-fluoro-3-oxo-4-phenylbutanoate was formed (yield: 73%).

This organic layer was concentrated under reduced pressure, and the concentrate was isolated by silica gel column chromatography (Wako gel C-200, eluted by hexane:ethyl acetate=8:2) to obtain 1.46 g of ethyl 4-fluoro-3-oxo-4-phenylbutanoate.

Mass analysis value: CI-MS m/e=225 (m+1)

$^1$H-NMR (CDCl$_3$) δ (ppm): 1.21 to 1.33 (3H, m), 3.51 to 3.70 (1.6H, m), 4.13 to 4.26 (2H, m), 5.48 (0.2H, s), 5.70 to 5.93 (1H, dd), 7.40 (5H, s), 12.02 (0.2H, s)

According to $^1$H-NMR analysis, it could be confirmed to exist a keto-enol form.

Example 8

Synthesis of ethyl 4-fluoro-3-oxooctanoate

To a liquor in which 2.38 g of 63.7% sodium hydride was suspended in 28 ml of tetrahydrofuran was added dropwise a mixed solution comprising 5.59 g of ethyl 2-fluorohexanoate and 4.16 g of ethyl acetate over 40 minutes, and the mixture was then heated at 45 to 50° C. for 2 hours.

After completion of the reaction, the mixture was cooled to room temperature, neutralized with 1N-hydrochloric acid and the liquids were separated. The organic layer was quantitated by the gas chromatography internal standard method to find out that 3.87 g of ethyl 4-fluoro-3-oxooctanoate was formed (yield: 55%).

This organic layer was concentrated under reduced pressure, and distilled under reduced pressure to obtain 3.17 g of ethyl 4-fluoro-3-oxooctanoate.

Boiling point: 73 to 75° C./3 to 4 mmHg

Mass analysis value: CI-MS m/e=205 (m+1)

$^1$H-NMR (CDC$_3$) δ (ppm): 0.90 to 0.95 (3H, m), 1.26 to 1.53 (7H, m), 1.74 to 1.96 (2H, m), 3.57 to 3.69 (1.84H, m), 4.19 to 4.25 (2H, m), 4.76 to 5.03 (1H, m), 5.30 (0.08H, s), 11.80 to 12.20 (0.08H, bs)

According to $^1$H-NMR analysis, it could be confirmed to exist a keto-enol form.

Example 9

Synthesis of ethyl 4-fluoro-2-methyl-3-oxopentanoate

To a liquor in which 3.13 g of 63.7% sodium hydride was suspended in 25 ml of tetrahydrofuran was added dropwise a mixed solution comprising 5.02 g of ethyl 2-fluoropropionate and 6.40 g of ethyl propionate over 30 minutes, and the mixture was then heated at 40 to 45° C. for 2 hours.

After completion of the reaction, the mixture was cooled to room temperature, neutralized with 1N-hydrochloric acid and the liquids were separated. The organic layer was quantitated by the gas chromatography internal standard method to find out that 5.27 g of ethyl 4-fluoro-2-methyl-3-oxopentanoate was formed (yield: 72%).

This organic layer was concentrated under reduced pressure, and distilled under reduced pressure to obtain 2.25 g of ethyl 4-fluoro-2-methyl-3-oxopentanoate.

Boiling point: 82 to 83° C./17 to 18 mmHg

Mass analysis value: CI-MS m/e=177 (m+1)

$^1$H-NMR (CDCl$_3$) δ (ppm): 1.25 to 1.29 (3H, m), 1.35 to 1.39 (3H, m), 1.46 to 1.62 (3H, m), 3.83 to 3.89 (1H, m), 4.17 to 4.25 (2H, m), 4.91 to 5.17 (1H, m)

Reference Example 1

Synthesis of 6-(1-fluoroethyl)-4-pyrimidone

To a solution in which 9.33 g of methyl 4-fluoro-3-oxopentanoate dissolved in 115 ml of methanol were successively added 36.5 g of a 28% sodium methoxide methanol solution, and 9.84 g of formamidine acetate at room temperature, and then, the mixture was stirred at 40° C. for 12 hours.

Moreover, 0.66 g of formamidine acetate was additionally added and the mixture was stirred at 50° C. for 2 hours. Then, the mixture was cooled to 10° C. or lower, and a mixture comprising 9.51 g of conc. sulfuric acid and 8.5 g of water was added to the above mixture.

After stirring at 50° C. for 30 minutes, insoluble materials were filtered off, and the filtrate was quantitated by the liquid chromatography internal standard method to find out that 7.99 g of 6-(1-fluoroethyl)-4-pyrimidone was formed (yield: 89.2%).

The filtrate was concentrated under reduced pressure, and the concentrated solution was recrystallized from 40 ml of isopropanol to obtain 5.82 g of 6-(1-fluoroethyl)-4-pyrimidone.

Melting point: 170 to 171.50° C.

Mass analysis value: CI-MS m/e=143 (m+1)

$^1$H-NMR (CDCl$_3$) δ (ppm): 1.60 to 1.67 (3H, dd), 5.34 to 5.47 (1H, dq), 6.62 to 6.63 (1H, t), 8.13 (1H, s), 13.3 (1H, br)

Reference Example 2

Synthesis of 5-chloro-6-(1-fluoroethyl)-4-pyrimidone

Sulfuryl chloride (2.45 g) was added to a solution in which 1.29 g of 6-(1-fluoroethyl)-4-pyrimidone dissolved in 15 ml of N,N-dimethylformamide, and the mixture was stirred at 50° C. for 3 hours.

When the reaction mixture was quantitated by the liquid chromatography internal standard method, 1.52 g of 5-chloro-6-(1-fluoroethyl)-4-pyrimidone was found to be formed (yield: 95.0%).

The reaction mixture was concentrated under reduced pressure and the concentrated solution was recrystallized from 3 ml of isopropanol to obtain 1.32 g of 5-chloro-6-(1-fluoroethyl)-4-pyrimidone.

Melting point: 190 to 191° C.

Mass analysis value: CI-MS m/e=177 (m+1)

$^1$H-NMR (CDCl$_3$) δ (ppm): 1.49 to 1.60 (3H, dd), 5.76 to 6.00 (1H, dq), 8.27 (1H, s), 13.15 (1H, br)

Reference Example 3

Synthesis of 4,5-dichloro-6-(1-fluoroethyl) pyrimidine

To a liquor in which 1.00 g of 5-chloro-6-(1-fluoroethyl)-4-pyrimidone was suspended in 10 ml of 1,2-dichloroethane were added one drop of N,N-dimethylformamide and 0.81 g of thionyl chloride, and the mixture was refluxed for 2 hours.

The reaction mixture was washed with 10 ml of water, and the organic layer was quantitated by the liquid chromatography internal standard method to find out that 1.09 g of 4,5-dichloro-6-(1-fluoroethyl)pyrimidinewas formed (yield: 98%).

The organic layer was concentrated under reduced pressure, and distilled under reduced pressure to obtain 0.76 g of 4,5-dichloro-6-(1-fluoroethyl)pyrimidine.

Boiling point: 84 to 88° C./5 mmHg

Mass analysis value: CI-MS m/e=195 (m+1)

$^1$H-NMR (CDCl$_3$) δ (ppm): 1.66 to 1.78 (3H, dd), 5.89 to 6.14 (1H, dq), 8.92 (1H, s)

Utilizability in Industry

The novel 4-fluoro-3-oxocarboxylates of the present invention are an important synthetic intermediate for aminopyrimidine derivatives useful as an insecticide, acaricide, fungicide or nematocide.

What is claimed is:

1. 4-Fluoro-3-oxocarboxylates represented by the following formula (1):

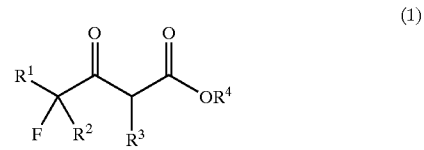

wherein $R^1$ represents an alkyl group or an aryl group;

$R^2$ and $R^3$ each represent a hydrogen atom or an alkyl group;

and $R^4$ represents an alkyl group.

2. The 4-fluoro-3-oxocarboxylates according to claim 1, wherein $R^1$ is an alkyl group having 1 to 10 carbon atoms or a phenyl group; $R^2$ and $R^3$ are each a hydrogen atom or an alkyl group having 1 to 10 carbon atoms; and $R^4$ is an alkyl group having 1 to 10 carbon atoms.

3. The 4-fluoro-3-oxocarboxylates according to claim 1, wherein $R^1$ is an alkyl group having 1 to 4 carbon atoms or a phenyl group; $R^2$ and $R^3$ are each a hydrogen atom or an alkyl group having 1 to 4 carbon atoms; and $R^4$ is an alkyl group having 1 to 4 carbon atoms.

4. The 4-fluoro-3-oxocarboxylates according to claim 1, wherein $R^1$ is a methyl group, an ethyl group, a propyl group, a butyl group or a phenyl group; $R^2$ is a hydrogen atom or a methyl group; $R^3$ is a hydrogen atom or a methyl group; and $R^4$ represents a methyl group, an ethyl group or a butyl group.

5. A process for preparing 4-fluoro-3-oxocarboxylates represented by the formula (1) defined in claim 1, which comprises allowing a 2-fluorocarboxylate represented by the following formula (2):

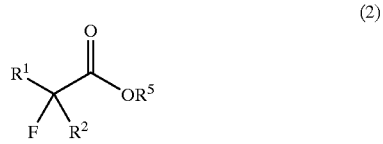

wherein $R^1$ and $R^2$ have the same meanings as defined in claim 1, and $R^5$ represents an alkyl group, to react with a carboxylate represented by the following formula (3):

wherein $R^3$ and $R^4$ have the same meanings as defined in claim 1, in the presence of a base of an alkali metal hydride.

6. A The process for preparing 4-fluoro-3-oxocarboxylates according to claim 5, wherein $R^5$ is an alkyl group having 1 to 10 carbon atoms.

7. The process for preparing 4-fluoro-3-oxocarboxylates according to claim 5, wherein the base is selected from the group consisting of lithium hydride, sodium hydride and potassium hydride.

8. The process for preparing 4-fluoro-3-oxocarboxylates according to claim 5, wherein in compound (3) is used in an amount of 1 to 3-fold mol based on the amount of the compound (2).

\* \* \* \* \*